United States Patent [19]

Gardiner et al.

[11] 4,456,375
[45] Jun. 26, 1984

[54] OPTICAL DISC MEASUREMENT BY REFRACTION

[75] Inventors: Mark E. Gardiner, Westwood; David W. Kuntz, Pacific Palisades, both of Calif.

[73] Assignee: Discovision Associates, Costa Mesa, Calif.

[21] Appl. No.: 324,341

[22] Filed: Nov. 23, 1981

[51] Int. Cl.³ ............................................. G01N 21/88
[52] U.S. Cl. ...................................... 356/239; 369/58
[58] Field of Search ................ 356/237, 239; 369/54, 369/58

[56] References Cited

U.S. PATENT DOCUMENTS

| | | | |
|---|---|---|---|
| 3,964,830 | 6/1976 | Ikeda et al. | 356/237 X |
| 4,153,336 | 5/1979 | Minami et al. | 356/239 X |
| 4,341,469 | 7/1982 | Gardiner et al. | 356/239 X |

Primary Examiner—Vincent P. McGraw
Assistant Examiner—L. A. Dietert
Attorney, Agent, or Firm—Ronald J. Clark

[57] ABSTRACT

A method for measuring the size of dimple-type defects in an area of the surface of a flat piece of transparent material, such as an optical disc. A large beam of collimated light is provided and passed through the piece of material in a normal orientation with respect to the surface being inspected. A screen is placed in the path of the beam emerging from the disc and circular shadows generated by refraction are measured to determine the size of the defects which produces them.

8 Claims, 11 Drawing Figures

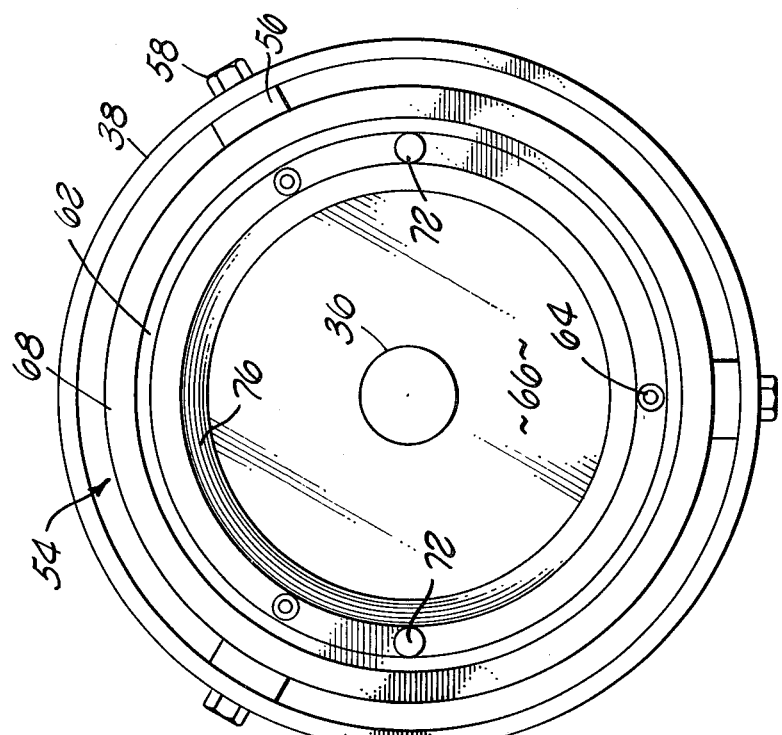
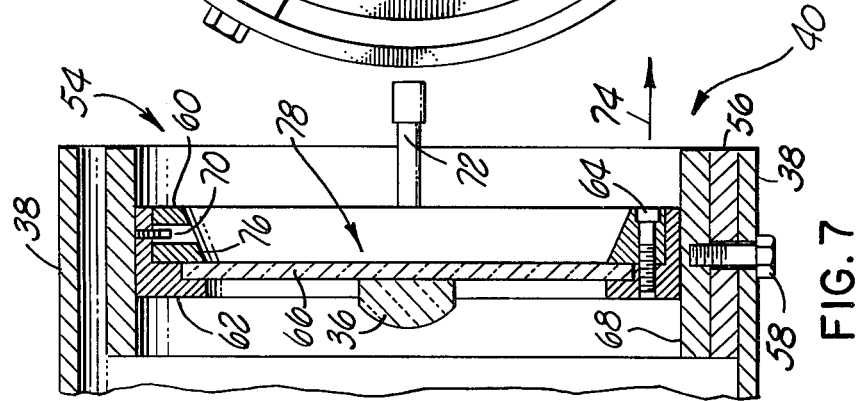
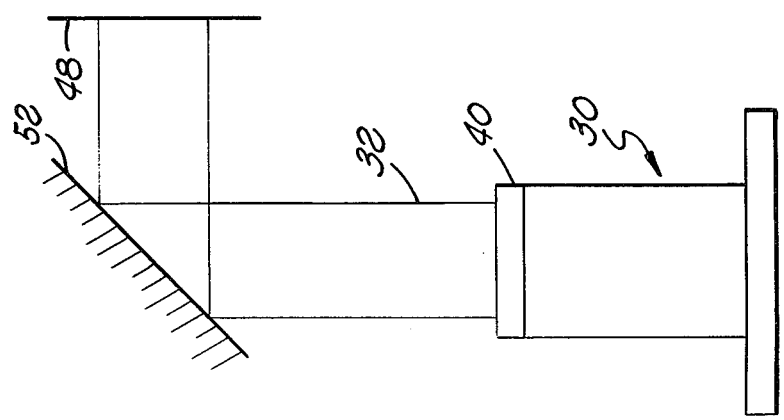

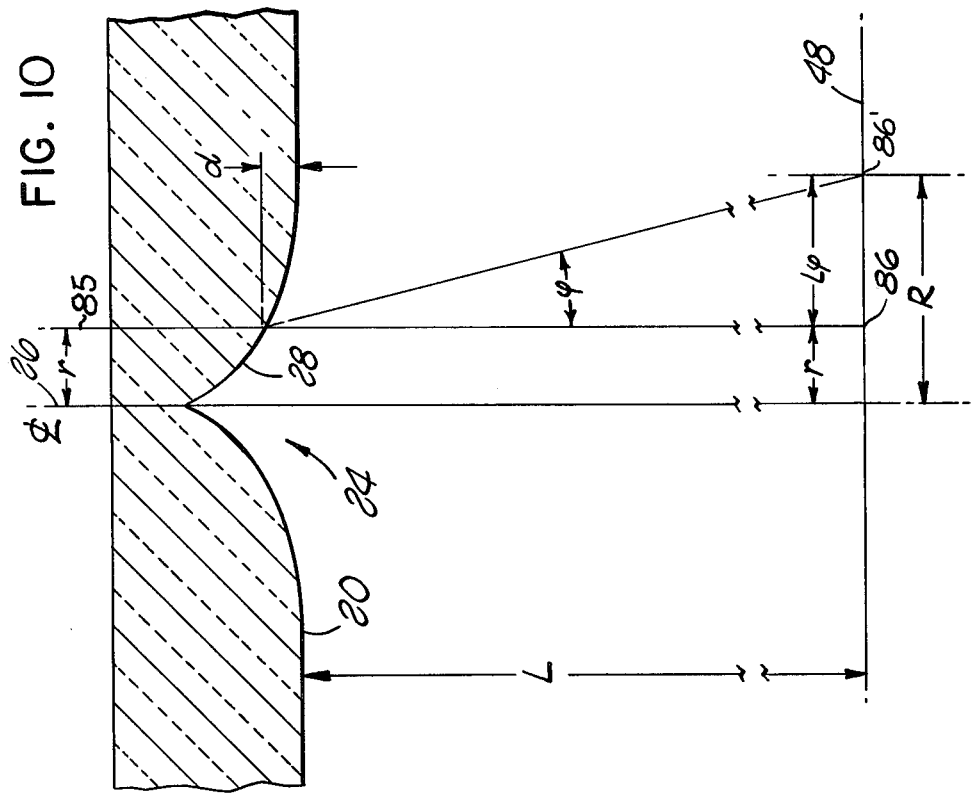
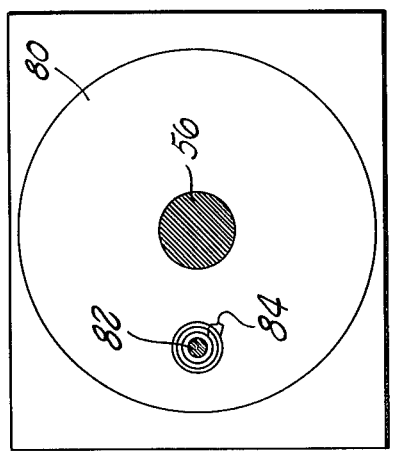
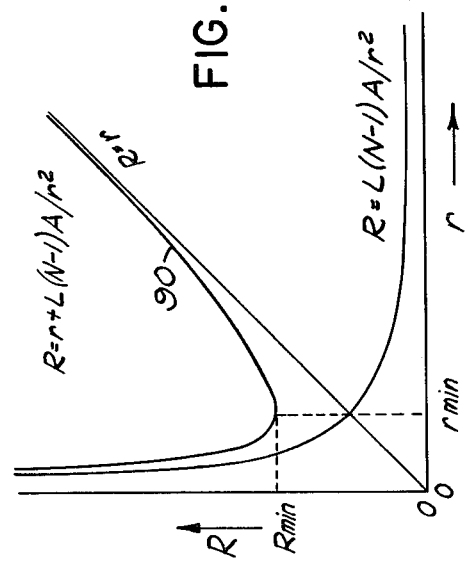

OPTICAL DISC MEASUREMENT BY REFRACTION

BACKGROUND OF THE INVENTION

1. Field of the Invention

The present invention relates to the measurement of defects in optical discs, and more particularly relates to the measurement of small local irregularities on the information surface of optical discs.

2. Brief Description of the Prior Art

An optical disc is a flat disc approximately the size of an LP phonograph record, made of transparent material, in which information is stored in tracks on a recording surface embedded in the interior of the disc. The tracks comprise a sequential series of tiny indicia exhibiting optical contrast with respect to the recording surface in which the tracks are formed. Information is recovered from the tracks by scanning a spot of light along the tracks and detecting the variations in the reflected light produced by the optical contrast of the indicia. Typically, the optical contrast of the indicia is exhibited as a difference in the level of reflectance of the indicia as compared with the surrounding recording surface. The optical disc has a very high density information storage capability and is used commercially for the recording and playback of video program material.

The recording surface of an optical disc must be kept quite flat to allow for error free playback of information stored on the surface. For example, a defect of even microscopic size in a video optical disc can disrupt the playback of the video program information, causing picture dropout, skipping from frame to frame, and other unacceptable playback problems.

In the manufacture of optical discs, therefore, it is desirable to have a way of detecting and measuring such defects. It is also desirable to be able to detect such defects rapidly so that defect detection can be applied economically to the disc manufacturing process.

In the field of video optical disc manufacture, defect detection has taken two forms. According to one approach, finished optical discs are taken off of the assembly line and simply played on an optical disc player apparatus. The recovered video picture is monitored, and when a video picture of unacceptable quality is observed, the disc is rejected. This approach is extremely expensive in man hours if the entire playing surface of every optical disc manufactured is examined in this way.

The second approach involves projecting one or more narrow beams of light onto the recording surface, and detecting variations in the beam of light which is reflected off of that surface. Copending U.S. patent application Ser. No. 300,364, commonly assigned to the assignee of the present invention, describes one such technique in which a conventional optical disc player apparatus is modified to provide an auxiliary beam specially arranged so that deviations in the position of the reflected beam can be detected and related to the presence and size of defects on the information surface of the optical disc.

This second approach represents an improvement over the first approach in that such a modified player apparatus can be played in a fast scan mode to inspect an optical disc for defects in a much shorter time then it takes to play the entire disc through. It is desired, however, to provide an even more rapid way of examining optical discs for defects to reduce even further the time spent in quality control inspection in the disc manufacturing process.

The present invention provides this improvement.

SUMMARY OF THE INVENTION

The present invention resides in a method for measuring the size of dimple-type defects in an area of the surface of a flat piece of transparent material, for example the recording surface of an optical disc. A beam of collimated light is provided having a cross sectional size and configuration comparable to the area on the surface of the transparent plate which is to be inspected.

For example, in the case of an optical disc, the information surface of the disc occupies a large, annular area. The cross section of a beam of collimated light provided to inspect such a disc is preferably circular or annular in configuration and large enough to include the annular information surface area of the disc.

The beam is directed through the plate in a direction substantially perpendicular to the plane of the surface being inspected, and a screen is provided in the path of the beam on the opposite side of the surface being inspected. The beam impinges on the screen and produces a bright field thereon. Dimple-type defects present in the disc refract the light of the beam and produce circularly-shaped shadows in the bright field. The dimensions of these circularly-shaped shadows are measured and related to the size of the dimple defects which produce them to ascertain the dimensions of the defects. Accurate correlations of the dimensions of the shadows to the sized defects may be derived to obtain accurate measurements of the defects.

Using the above procedure, the present invention provides a rapid method for screening acceptable optical discs from unacceptable ones. For example, in the case of optical discs bearing video program information, the existence of dimple-type defects having a dimension greater than a specified dimension may be correlated with video playback disturbances considered to be unacceptable. By applying the principles of the present invention to the inspection of completed discs as they come off of the production line, the discs may be rapidly tested and screened for probability of acceptability for playback.

It will therefore be appreciated that the present invention provides a quick method for inspecting the quality of surfaces of transparent plates, such as optical discs, and can provide accurate measurements of the size of dimple-type defects on the surface of the plate. The present invention introduces considerable cost savings in the manufacture of high quality transparent information discs such as optical discs by reducing the cost of playability testing of such discs as they come off of the production line. Other aspects and advantages of the present invention will become apparent from the following detailed description, taken in connection with the accompanying drawings.

BRIEF DESCRIPTION OF THE DRAWINGS

FIG. 6 is a diagram of the optical arrangement of the preferred embodiment of the present invention.

FIG. 7 is a partial cross-section view of the optical apparatus of FIG. 4 showing the support frame thereof in greater detail.

FIG. 8 is an end view of the optical apparatus of FIG. 4 from which the collimated light emerges, showing the support frame thereof.

FIG. 9 is a plan view of a screen showing a bright field produced in accordance with the principles of the present invention.

FIG. 10 is a view similar to that shown in FIG. 3, also showing certain geometric relationships with respect to a screen.

FIG. 11 is a graph showing a plot of an equation utilized in conjunction with the preferred embodiment of the present invention.

DETAILED DESCRIPTION OF THE PREFERRED EMBODIMENT

Figure 1:
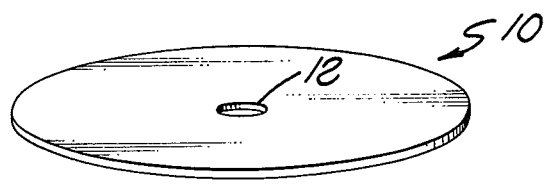
FIG. 1 if an orthogonal view of an optical disc.

FIG. 1 is an orthogonal view of an optical disc 10. The disc 10 is flat and circular, approximately the size and shape of an LP phonograph record, and made of clear plastic. An aperture 12 is provided at the center of the disc to allow the disc to be placed on a spindle (not shown) for high speed rotation for reading in the information contained therein.

Figure 2:
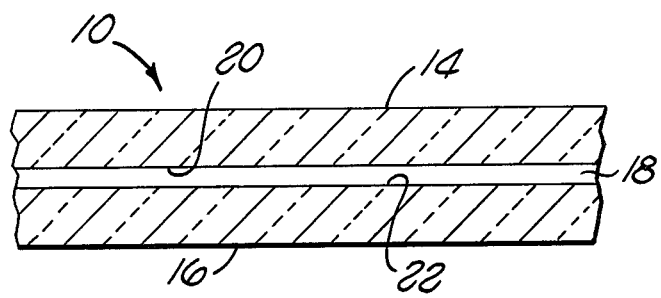
FIG. 2 is partial section view through the optical disc of FIG. 1.

FIG. 2 is a partial cross-section of the disc 10 shown in FIG. 1. The disc 10 is made from two disc parts 14 and 16 separated by a small gap 18 which may, for example, be filled with the adhesive substance used to hold the two parts 14, 16 together. Information is stored in the disc 10 on the interior surfaces 20, 22 of the two parts 14, 16, of the disc. The information is typically stored in the form of tracks of sequentially spaced indicia having optical contrast with respect to the surrounding surface in which the indicia are formed.

The disc 10 is read by imaging a beam of light to a tiny spot through the transparent material of one of the parts 14, 16 of the disc to an infomation track on one of the reflective surfaces 20 or 22, rotating the disc to cause the spot of light to scan along the track, and detecting the light which is reflected off of the surface and modulated by the alternate presence and absence of the indicia along the track.

Player apparatus for such discs typically include a tracking servo system for maintaining the imaged spot centered on the information track as it is read by the apparatus, and a focus servo system for maintaining the spot of light in focus on the track. Such servo systems can maintain the spot of light in focus and centered on the track despite small and gradual variations in the flatness of the information surface in which the track is formed. However, large and abrupt deviations in flatness of the surface, for example due to microscopic defects, can cause a servo to exceed its limits, and the spot of light may defocus or leave the desired track, giving rise to interruptions in the flow of information as it is retrieved from the disc. Such interruptions represent a serious problem, and discs having this problem are usually considered unusable for video playback purposes.

Figure 3:
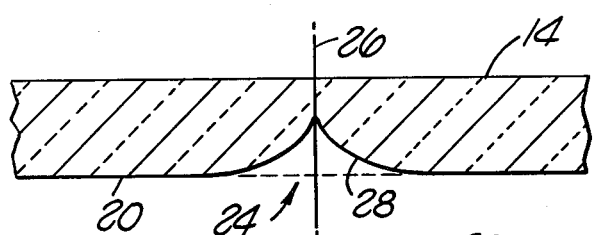
FIG. 3 is a partial cross-section view through one of the two parts that make up the optical disc of FIG. 1, showing a dimple-type defect therein.

One common form of defect which gives rise to variations in the flatness of the information surface great enough to cause the tracking and focus servos to exceed their limits is the "dimple." FIG. 3 is a cross-sectional view of a portion of the disc part 14 taken though the center of a dimple defect 24. The dimensions of the dimple 24 with respect to the thickness of the disc part 14 have been greatly exaggerated for the purpose of illustration. Such a disc part 14 is actually several millimeters thick, while a dimple may be 10 microns in depth. The configuration of the surface of the dimple 24 is typically symmetrical about a center line 26. It will be appreciated that the slope of the side 28 of the dimple 24 causes the aforementioned reflected light from an imaged beam of light to be deflected from its normal path. This light deflection is what causes the aforementioned loss of servo tracking and resulting information loss.

In view of the foregoing, it will be appreciated that the slope of the side 28 of a dimple 24 can be related directly to an unwanted deflection of the reading beam of light. In fact, the size of a dimple defect can be correlated with information loss such that if the dimensions of a dimple defect on a disc are known, it can be ascertained with a high degree of probability whether the disc will provide acceptable information retrieval for a player apparatus of a known quality. The present invention provides a means for ascertaining the dimensions of such dimple defects.

Figure 4:
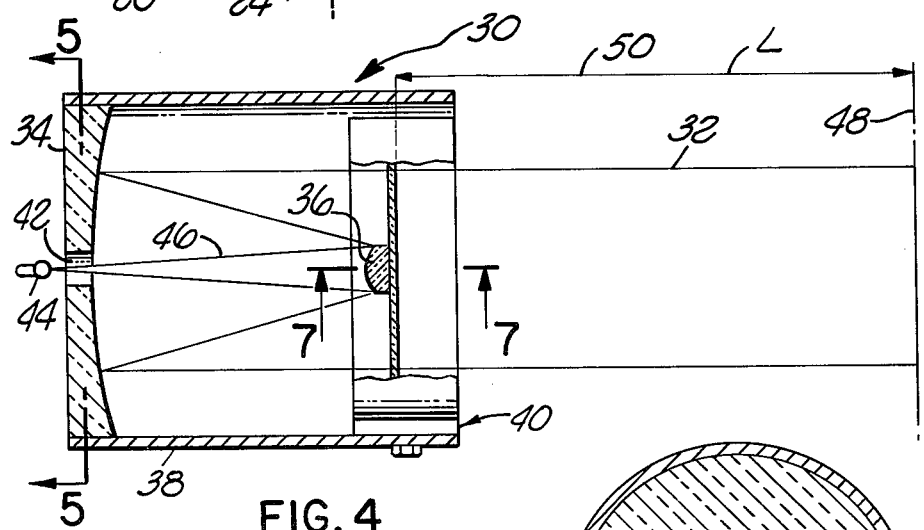
FIG. 4 is a section view of an optical arrangement constructed according to the principles of the present invention.

FIG. 4 is a cross-sectional view through an apparatus constructed according to the principles of the present invention illustrating the basic principles of operation. The apparatus is an optical system which is used to detect the existence and size of dimple defects in a disc, such as described in connection with FIG. 3. The apparatus 30 is a large Cassegrain optical system for producing a large diameter circular cross section collimated light beam 32. The optical system 30 includes a primary reflector mirror 34, having a diameter of approximately 12.5 inches, and a secondary reflecting mirror 36. The two mirrors, 34, 36 are supported by a large cylindrical housing 38. A support frame 40 is provided at the end of the housing 38 near the secondary mirror 36. This support frame 40 is used to support an optical disc (not shown) which may be placed therein, and to maintain the disc oriented in a plane normal to the central axis of the beam of light 32. The primary mirror 34 is provided with a small opening 42 through which the light from a small, high intensity lamp 44 is directed in a narrow, diverging beam 46 to the secondary mirror 36 which directs the beam 46 back to substantially fill the primary mirror 34. The primary mirror 34 reflects the beam of light 32 back in the direction of the secondary mirror 36 as a collimated beam of light 32. The principles of construction and operation of a Cassegrain optical system are well known in the field of optics, for example for astronomical observation, and therefore will not be described in detail herein.

The collimated beam of light 32 passes through the disc support area of the frame 40 and impinges on a screen 48, such as a conventional projection screen, which is placed in its path. The screen 48 is placed at a distance L from the plane of the disc held in the frame 40, as shown by arrow 50 in FIG. 4.

Figure 5:
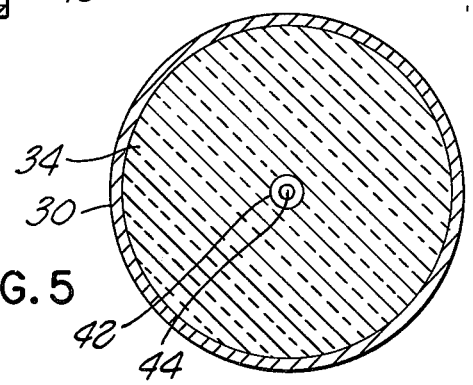
FIG. 5 is a section view through lines 5—5 of FIG. 4.

FIG. 5 is a sectional view through line 5—5 of FIG. 4, showing the large, annularly-shaped primary mirror 34, supported by the cylindrical housing 30. The small, high intensity light 44 can be seen centered in the hole 42 in primary mirror 34.

FIG. 6 is a block diagram depicting the optical arrangement of the preferred embodiment of the present invention. According to the preferred embodiment, the optical system 30 is oriented such that the axis of the emergent beam of collimated light 32 is in the vertical direction. A mirror 52 is placed in the path at approximately a 45° angle, which directs the emergent collimated beam 32 to the screen 48, which is also vertically aligned, as shown. This permits the support frame 40 of the preferred embodiment to be effectively utilized, in a manner which will now be described.

FIG. 8 is an end view of the optical system 30 showing the details of the support frame 40 of the preferred embodiment. FIG. 7 is a section view showing the support frame 40 of FIG. 8. Referring to both figures together, the support frame 40 comprises a disc support assembly which is supported on the interior of the housing 38 by way of three spacers 56 arranged at intervals of approximately 120° around the interior of the housing 38 through which bolts 58 extend and screw into the disc support assembly 54. The disc support assembly 54 comprises a retainer 60 and mount 62, which are bolted together by way of bolts 64, and which support a glass plate 66. The mount 62 is slidably engaged with the interior of a guide ring 68 which forms the exterior elements into which the mounting bolts 58 are screwed. Three set screws 70 also arranged at positions 120° spaced from one another secure the mount 62 to the guide ring 68 when the mount 62 is properly oriented. Two bars 72 serve as handles for moving the mount 62 within the guide ring 68.

In practice, the optical assembly 30 is oriented in a vertical direction, as was mentioned previously in connection with FIG. 6, such that the support frame 40 faces upward as depicted by arrow 74 in FIG. 7. It will be noted that the retainer 60 is provided with an angular beveled surface 76. The diameter of the innermost portion of the retainer 60 is just slightly larger than the outer diameter of a disc, which is to be inspected using the apparatus. When a disc is placed in the opening 78 formed by the retainer 60, the beveled surface 76 guides the disc to a centered position resting on the piece of glass 66 which serves to support and orient the disc. The mount 62 is adjusted such that the centered, supported disc is oriented such that the surface to be inspected is substantially perpendicular to the central axis of the beam of collimated light. In this way, the preferred embodiment is especially adapted for rapid, assembly line inspection of discs in that once the mount is adjusted and set a disc may be merely placed roughly within the opening 78, and the support frame 40 will serve to quickly and automatically center the disc and orient the disc in a perpendicular configuration with respect to the central axis of the optical system 30. The plate of glass 66 serves as a support for the secondary mirror 36, which is attached to the piece of glass 66 by gluing, and as a support for a disc, as well as described below.

FIG. 9 is a view of the screen 48 showing the bright field 80 from the collimated beam of light 32 (FIG. 4) incident thereon. The aforementioned shadow 56 from the secondary mirror 36 (FIG. 4) can be seen in the field 80. A dark, circular refraction shadow 82 of the kind produced by the presence of a dimple-type defect in an optical disc is present in the field 54. As can be seen, the dark, circular shadow 82 is surrounded by a series of bright and dark rings 84. The configuration of the shadow 82 and associated concentric rings 84 is characteristic for the refraction pattern produced by a dimple-type defect in an optical disc placed in the path of a collimated beam of light as discussed above in connection with FIG. 4. Thus, it will be appreciated that the optical configuration described herein provides a technique for detecting the presence of such optical defects in optical discs. In addition, the size of such defects may be derived in accordance with the principles discussed below.

FIG. 10 is a cross-sectional view of a disc part 14, identical to that shown in FIG. 3. FIG. 10 also shows a side view of the screen 48 with respect to the disc part 14 when arranged in the configuration shown in FIG. 4. It will be appreciated that relative to the thickness of the disc part 14, the screen 48 is at a much greater distance from the plate part 14 than shown in FIG. 10. The preferred distance is one meter.

A ray 85 of light from the collimated beam 32 (FIG. 4) is shown passing through the disc part 14 to the screen 48. As can be seen, the ray 85 is deflected at the side 28 of the dimple 24 due to the angle presented by the slope of the side 28 and the difference in the refractive index between the plastic of the disc part 14 and the surrounding material. In examining discs for dimple-type defects, the two parts of each disc are examined separately, and thus the surrounding material is typically air, which has a refractive index of 1. The deflection angle $\phi$, gives rise to a deflection of the location of impingement of the light ray 85 on the screen 48 from point 86 to point 86', equal to a distance $L\phi$, as shown. Thus, from the geometry of the configuration, the radial distance R of the point 86' from the center line 26 can be related to the radial distance r from the center line 26 of the undeflected ray of light 24. Thus, $$R = r + L\phi.$$

The angular deflection $\phi$ can be expressed mathematically. The formula is derived as follows.

To begin with, it has been discovered that the depth h of the surface 28 of the dimple 24 from the surrounding information surface 20, shown in FIG. 10, can be related to the radial distance r of a point on the surface 28 by the expression $$h = A/r \qquad (1)$$

where A is a constant representative of the size of the particular dimple being measured.

Therefore, the slope of the surface 28 can be expressed by the formula:

$$dh/dr = -A/r^2 = \text{slope of dimple} \qquad (2)$$

Applying known principles of optics, and assuming that the index of refraction of the gap material is equal to unity, the angle $\phi$ through which the light ray 85 (FIG. 10) is deflected is expressed approximately as the following:

$$\phi \simeq (N - 1) \text{ (slope of dimple)} \qquad (3)$$
$$= (N - 1) (A/r^2),$$

where N equals the index of refraction of the disc part 14.

From the geometry of FIG. 10, $$R = r + L\phi. \qquad (4)$$

Therefore, $$R = r + L(N-1)A/r^2. \quad (5)$$

FIG. 11 is a graph showing a plot 90 of expression (5), as well as of component curves R r and $R = L(N-1)A/r^2$ to illustrate the asymptotes of the plot 64.

From FIG. 11, it will be appreciated that the plot 90 has a minimum value of R, namely $R_{min}$, occurring for a ray 85 (FIG. 10) located a distance $r_{min}$ from the centerline 26. Thus, for rays of light incident on the disc part 14 at an orientation normal to the information surface 20 of part 14, no light will be incident on the screen 48 a distance less than $R_{min}$ from the point of intersection 66 of the centerline 26 with the screen 48. In other words, a dimple 24 will cause a circular shadow of radius $R_{min}$ in the bright field of a collimated beam of light that passes through the disc part 14 in which the dimple 24 is formed at an orientation normal to the surface of the disc part 14.

Returning now to FIG. 9, it will be appreciated that a measurement of the circular shadow 82 can provide a determination of dimensions of the dimple which produced the shadow.

Specifically, referring to expression (5), above, $R_{min}$ can be found by setting dR/dr equal to zero. This gives the following expression:

$$0 = 1 - 2L(N-1)A/r^3. \quad (6)$$

This yields:

$$r_{min} = [2L(N-1)A]^{\frac{1}{3}} \quad (7)$$

from which it can be determined that $$\begin{aligned} R_{min} &= (2^{\frac{1}{3}} + 2^{-\frac{2}{3}})[L(N-1)A]^{\frac{1}{3}} \\ &= 2.053[L(N-1)A]^{\frac{1}{3}}. \end{aligned} \quad (8)$$

From this, $$A = \frac{R_{min}^3}{8.661(L)(N-1)}. \quad (9)$$

It will be recalled from the discussion in connection with FIG. 10 that the quantity A provides an expression of the characteristics of a dimple 24 in that $$h = A/r.$$

Thus it has been shown that by measuring the radius of a circular shadow produced in the field of light on a screen, produced in accordance with the principles of the present invention, a measurement of the dimensions of a dimple-type defect may be obtained.

Even in the absence of the application of precise mathematical principles as described above, correlation may be derived between the size of dimple defects and circular diffraction patterns, produced in accordance with the principles of the present invention, by empirical methods. For example, using conventional measurement techniques, such as by using a Tallysurf apparatus, an exact measurement may be obtained of a dimple. It will be appreciated that such prior art measurement techniques may be time consuming, but once performed for a limited number of disc defects, the discs can be inspected by way of the present invention and an empirical correlation established. Once this correlation is established for a given optical arrangement constructed according to the present invention, measurements of additional defects on other discs may be obtained by applying the derived correlation relationship.

In addition, the measurement can be obtained quite rapidly as compared with prior art approaches, in that once the optical apparatus of the present invention is set up, a disc to be inspected is simply placed within the frame support, and the bright field produced on the screen is inspected for any circularly-shaped shadows. The shadows are measured, and the information concerning the dimples is thereby obtained. As compared with prior art approaches, wherein the disc must be scanned by a light beam, even in fast scan modes, the present invention provides a much more rapid method for obtaining information concerning dimples.

It will be appreciated from the foregoing that the present invention represents a significant advance in the field of surface irregularity measurement, especially as applied to the measurement of dimple-type defects in optical discs. In particular, the invention provides a rapid and highly accurate optical technique for applying a large beam of collimated light to an optical disc to obtain accurate information concerning the presence and size of dimple-type defects. It will also be appreciated that, although a specific embodiment of the invention has been described in detail for purposes of illustration, various modifications may be made without departing from the spirit and scope of the invention. Accordingly, the invention is not to be limited, except as by the appended claims.

We claim:

1. A method for detecting defects in an area to be inspected of the surface of a transparent plate of material, comprising the steps of:
   providing a beam of collimated light having a cross-sectional size comparable to the size of said area to be inspected;
   directing said beam through said plate in a direction substantially perpendicular to the plane of said surface;
   providing a screen in the path of said beam which emerges from said plate, such that the beam impinges on the screen in a bright field; and
   measuring the size of any circularly shaped shadows which occur in the field.

2. A method according to claim 1 further comprising the step of relating the measured size of the circularly shaped shadows to the size of the dimple defects which produce them.

3. Apparatus for measuring the size of dimple defects in an area to be inspected on the surface of a transparent plate of material, comprising:
   collimating means for providing a beam of collimated light having a cross-sectional size comparable to the size of said area to be inspected;
   support means for supporting said plate in the path of said collimated light beam such that the plane of said surface of said plate is oriented substantially perpendicular to the central axis of said beam and such that said area to be inspected intersects said beam; and
   a screen provided in the path of said beam which emerges from said plate, such that the beam impinges on the screen in a bright field.

4. Apparatus according to claim 3 wherein said support means is provided with centering means for centering said plate when said plate is placed in said support means.

5. Apparatus according to claim 4 wherein said collimating means is provided such that the central axis of said collimated beam of light is provided in a substantially vertical orientation, and wherein said centering means comprises means for centering a disc in said support by means of gravitational action.

6. Apparatus according to claim 5 wherein said support means comprises:
   a support surface for supporting the plate such that said surface is oriented substantially perpendicularly with respect to the central axis of said collimated beam of light; and
   a guide element having a surface which is provided at an angle with respect to the central axis of said beam of collimated light for guiding said disc onto said support surface through the action of gravity.

7. Apparatus according to claim 6 wherein said apparatus is intended for use in detecting defects on circular, disc-type plates, wherein said guide means further comprises means for guiding said discs to a centered configuration with respect to said collimated beam of light when said disc rests on said support surface.

8. Apparatus according to claim 5 further comprising a mirror, the reflective surface of which is oriented at an angle with respect to said collimated beam of light, and which is provided oriented substantially vertically in the path of the beam of light as it emerges from said mirror.

* * * * *